United States Patent [19]

Rao et al.

[11] Patent Number: 5,011,775
[45] Date of Patent: Apr. 30, 1991

[54] ENZYMATIC PROCESS FOR THE PREPARATION OF ROSMARINIC ACID

[75] Inventors: Nagaraj N. Rao, Bangalore, India; Christian Wandrey, Juelich, Fed. Rep. of Germany; Maike Petersen, Neuss, Fed. Rep. of Germany; August W. Alfermann, Erkrath, Fed. Rep. of Germany

[73] Assignee: Forschungszentrum Juelich GmbH, Juelich, Fed. Rep. of Germany

[21] Appl. No.: 448,130

[22] Filed: Dec. 13, 1989

[30] Foreign Application Priority Data

Dec. 13, 1988 [DE] Fed. Rep. of Germany ....... 3841914

[51] Int. Cl.$^5$ .................... C12P 7/40; C12P 7/56; C12P 7/62; C07C 69/732
[52] U.S. Cl. .................... 435/135; 435/146; 435/147; 435/190
[58] Field of Search ................. 435/146, 147, 135, 190

[56] References Cited

PUBLICATIONS

Petersen et al., "Two New Enzymes of Rosmarinic Acid Biosynthesis from Cell Cultures of Coleus blumei: Hydroxyphenylpyruvate Reductase and Rosmarinic Acid Synthase", Z. Naturforsch. 43 c: (1988) pp. 501-504.

Derwent Biotech Abs. 84-11669 De-Eknamkul et al., PLMEAA "Planta Med" (1984) 50, 4, 346-50.

Derwent Biotech Abs 86-09512 Ellis "Primary Secondary Metab Plant Cell Culture" (1985) 164-173.

Derwent Abs. 84-171729/29 DE3247610 (7-1984) Ulbricht et al.

Primary Examiner—Herbert J. Lilling
Attorney, Agent, or Firm—Foley & Lardner

[57] ABSTRACT

A process is disclosed for the production of rosmarinic acid of the formula

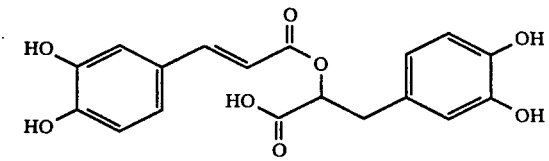

by enzymatic reaction of 3-(3,4-dihydroxyphenyl)-lactic acid with caffeoyl-coenzyme A in the presence of rosmarinic acid synthase. Ketodopa, which is readily accessible from dopa, is used as the starting material and caffeoyl-CoA is preferably regenerated by addition of caffeic acid.

15 Claims, 1 Drawing Sheet

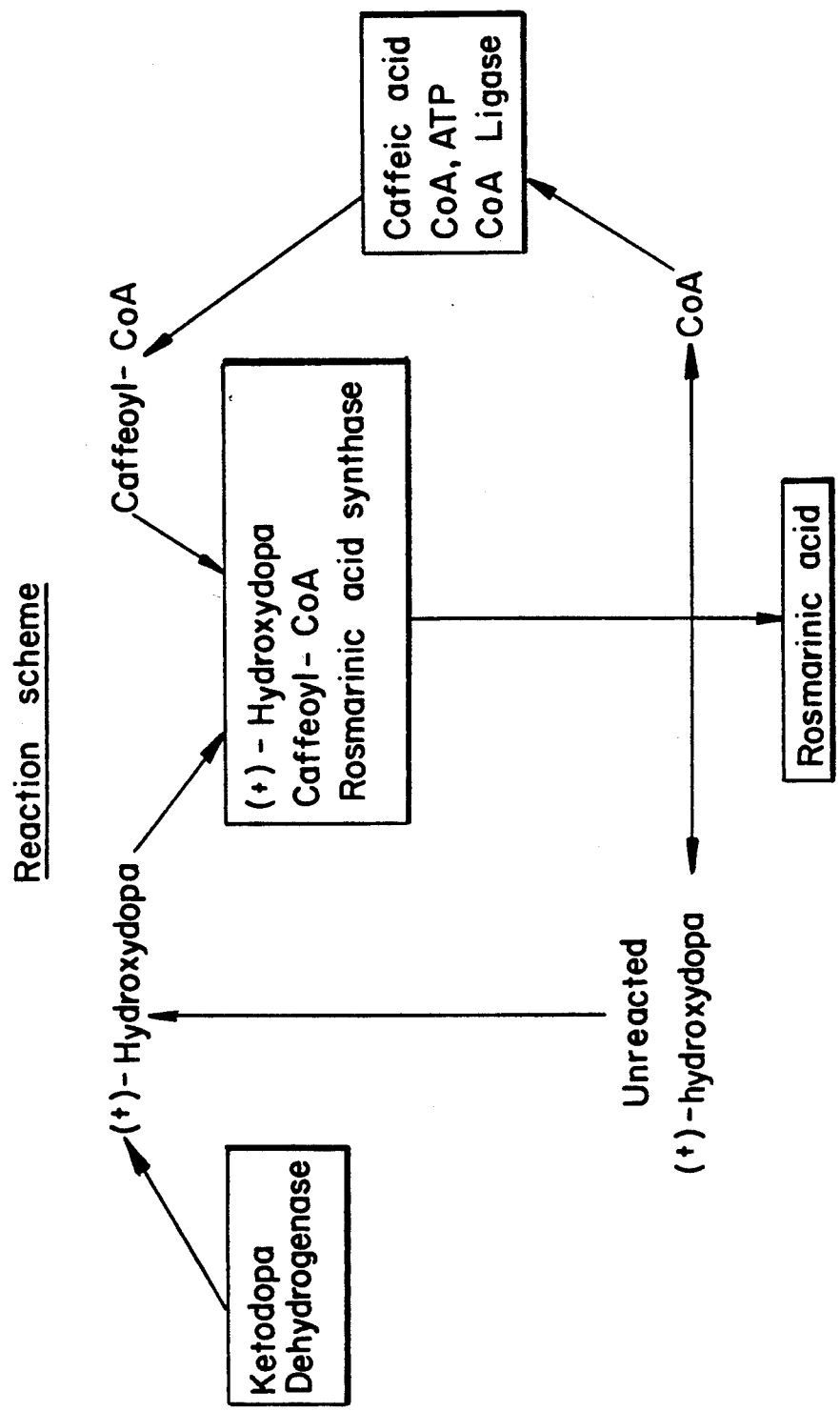

ENZYMATIC PROCESS FOR THE PREPARATION OF ROSMARINIC ACID

BACKGROUND OF THE INVENTION

The present invention relates to a process for the production of rosmarinic acid of the formula

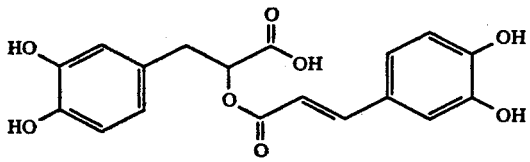

by enzymatic reaction of 3-(3,4-dihydroxyphenyl)-lactic acid with caffeoyl-coenzyme A in the presence of rosmarinic acid synthase.

The esters of nuclear-substituted cinnamic acids and nuclear-substituted phenyllactic acids have anti-inflammatory properties. Rosmarinic acid (RA), the ester from caffeic acid and the R(+)form of 3-(3,4-dihydroxyphenyl)-lactic acid, was obtained as a naturally occurring substance for the first time from the medicinal plant *Rosmarinus officinalis*. It has been the subject of intensive research for some years as a potential anti-inflammatory agent. RA has previously been, obtained either from plants or from plant cell cultures.

It has recently been found that cell cultures of *Coleus blumei* produce rosmarinic acid in considerable quantities. On extraction of the cell mass, M. Petersen and A.W. Alfermann (Z. *Naturforsch.* 43 c: 501–504 (1988)) isolated two enzymes and identified them based on their activity. A rosmarinic acid synthase was identified as the decisive enzyme for rosmarinic acid synthesis from caffeoyl-CoA and 3-(3,4-dihydroxyphenyl)-lactic acid. Dihydroxyphenylpyruvate reductase, with which the reduction of the keto acid to give the hydroxy acid is achieved in the presence of NADH, was also identified.

SUMMARY OF THE INVENTION

It is therefore an object of the present
process for synthesizing invention to provide a rosmarinic acid in which ketodopa readily accessible from dopa is used as the starting material and caffeoyl-CoA is preferably regenerated by addition of caffeic acid.

In order to achieve these and other objects according to the invention, a process is provided for the production of rosmarinic acid of the formula

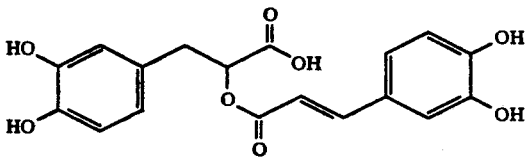

comprising the steps of forming 3-(3,4-dihydroxyphenyl)-lactic acid by enzymatic reduction of ketodopa in the presence of dehydrogenase and NADH$_2$, and enzymatically reacting 3-(3,4-dihydroxyphenyl)-lactic acid with caffeoyl-coenzyme A in the presence of rosmarinic acid synthase.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The single figure of drawing shows the reaction scheme for production of rosmarinic acid according to the present invention.

DETAILED DESCRIPTION OF THE PREFERRED EMBODIMENTS

The process according to the present invention consists essentially of previously or simultaneously forming 3-(3,4-dihydroxyphenyl)-lactic acid by enzymatic reaction of ketodopa in the dehydrogenase and NADH$_2$.

The dehydrogenase used here is, for example, D-lactate dehydrogenase, but in particular D-hydroxyisocaproate dehydrogenase.

The regeneration of caffeoyl-CoA by addition of caffeic acid, ATP and CoA ligase is carried out, in particular, in situ simultaneously with the rosmarinic acid synthesis.

Further details of the invention are provided by the following description with the aid of the accompanying diagram and the embodiment examples.

It can be seen from the diagram that the reaction of hydroxydopa and caffeoyl-CoA with rosmarinic acid synthase takes place to form a product solution, from which unreacted hydroxydopa on the one hand and coenzyme A on the other hand can be separated.

The unreacted hydroxydopa that is separated can be recycled directly to the synthesis, whereas the coenzyme A is reacted with caffeic acid, ATP and CoA ligase to give the caffeoyl-CoA required for the synthesis. This reaction (C) can proceed in the reaction mixture simultaneously with the rosmarinic acid synthesis reaction (A).

The production of hydroxydopa from ketodopa by means of dehydrogenase (reaction B) can precede reaction (A) or proceed directly in the reaction mixture A, as shown in the following Example 1.

EXAMPLE 1

Integrated process, batch set-up

Caffeoyl-CoA (10 mmol/l), D-hydroxyisocaproate dehydrogenase (5 units/ml) and rosmarinic acid synthase (1 unit/ml) are added to a solution of "ketodopa" (10 mmol/l) and NADH$_2$ (20 mmol/l) in TRIS-maleate buffer (25 mmolar) of pH 7.5, and the mixture is stirred for 8 hours. The proteins are separated by ultrafiltration, the filtrate is concentrated and the residue is extracted with ethyl acetate. This product solution is concentrated and rosmarinic acid, unreacted (+)hydroxydopa and ketodopa are separated from one another by means of preparative high performance liquid chromatography. Unreacted hydroxydopa and ketodopa are used again, as are the enzymes.

EXAMPLE 2

Integrated process, continuous set-up

A solution of "ketodopa" (30 mmol/l) and ammonium formate (100 mmol/l) in TRIS-maleate buffer (25 mmolar) of pH 7.5 is introduced continuously into an ultrafiltration cell with the possibility of stirring, for example, an Amicon cell. D-Hydroxyisocaproate dehydrogenase (20 units/ml), formate dehydrogenase (20 units/ml) and polymer-bound NADH$_2$ (for example PEG-NADH$_2$) (1 mmol/l) are previously introduced into the ultrafiltration cell. After a residence time of 2-3 hours, the mixture is analyzed by means of UV spectrophotometry and/or polarimetry and the conversion is determined.

Caffeic acid and ATP (in each case 30 mmol/l) are added to the discharged solution and the mixture is introduced into a second ultrafiltration cell containing rosmarinic acid synthase (5 units/ml), caffeoyl-CoA (30 mmol/l), ATP and CoA ligase (5 units/ml) in TRIS-maleate buffer (25 mmolar) of pH 7.5. After a residence time of 1 hour, the discharge is analyzed for rosmarinic acid and (+)-hydroxydopa and the components are separated by means of preparative high performance liquid chromatography. Unreacted (+)-hydroxydopa is used again.

EXAMPLE 3

Integrated process, semi-continuous set-up

A. As in Example 2, the product solution from the first stage is collected and reacted batchwise with caffeoyl-CoA, caffeic acid, ATP, rosmarinic acid synthase and CoA ligase (in the above-mentioned amounts) in an ultrafiltration cell.

B. As in Example 2, hydroxydopa is prepared in a batch set-up (see Example 1, but without caffeoyl-CoA and rosmarinic acid synthase) and the product solution is reacted as in the second part of the second example.

What is claimed is:

1. A process for the production of rosmarinic acid of the formula

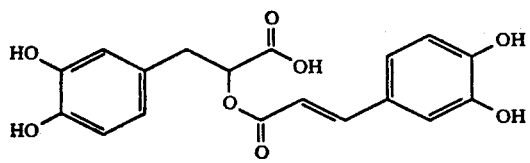

comprising the steps of:
forming 3-(3,4-dihydroxyphenyl)-lactic acid by enzymatic reduction of ketodopa in the presence of dehydrogenase and NADH$_2$,
enzymatically reacting 3-(3,4-dihydroxy-phenyl)-lactic acid with caffeoyl-coenzyme A in the presence of rosmarinic acid synthase to produce rosmarinic acid,
separating the rosmarinic acid produced from the unreacted 3-(3,4-dihydroxyphenyl)-pyruvic acid, 3-(3,4-dihydroxyphenyl)-lactic acid, dehydrogenase and rosmarinic acid synthase; and
recycling the unreacted 3-(3,4-dihydroxyphenyl)-pyruvic acid, 3-(3,4-dihydroxyphenyl)-lactic acid, dehydrogenase and rosmarinic acid synthase to the reaction mixture.

2. The process as claimed in claim 1, wherein the 3-(3,4-dihydroxyphenyl)-lactic acid is formed in the presence of D-hydroxyisocaproate dehydrogenase.

3. The process as claimed in claim 1 wherein the caffeoyl-CoA is regenerated in situ by the presence of caffeic acid, ATP and CoA ligase.

4. The process as claimed in claim 1, wherein the caffeoyl-CoA is regenerated in situ by the presence of caffeic acid, ATP and CoA ligase, and ATP is regenerated at the same time.

5. The process as claimed in claim 1, wherein the rosmarinic acid synthesis is carried out continuously in two stages by forming 3-(3,4-dihydroxyphenyl)-lactic acid from ketodopa in a first ultrafiltration cell and reacting the product stream from the first cell with caffeoyl-CoA, and simultaneously regenerating caffeoyl-CoA in a second ultrafiltration cell, to produce rosmarinic acid, which is isolated from the product stream of the second cell.

6. The process as claimed in claim 4, wherein ATP is regenerated with acetyl phosphate and acetylkinase.

7. The process as claimed in claim 1, wherein the 3-(3,4-dihydroxyphenyl)-lactic acid is formed before or during the enzymatic reaction.

8. An enzymatic process for the production of rosmarinic acid of the formula

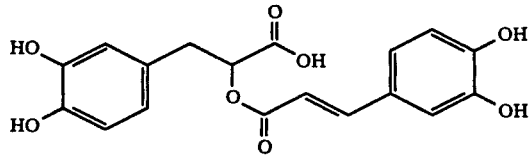

comprising the steps of:
providing a mixture of caffeoyl-coenzyme A, a dehydrogenase, rosmarinic acid synthase and NADH$_2$;
combining the mixture with a solution of 3-(3,4-dihydroxyphenyl)-pyruvic acid;
forming 3-(3,4-dihydroxyphenyl)-lactic acid by enzymatically reducing the 3-(3,4-dihydroxyphenyl)-pyruvic acid in a reaction catalyzed by the dehydrogenase in the presence of NADH$_2$;
enzymatically forming rosmarinic acid by reacting the 3-(3,4-dihydroxyphenyl)-lactic acid with the caffeoyl-coenzyme A in a reaction catalyzed by the rosmarinic acid synthase;
separating the rosmarinic acid produced from the unreacted 3-(3,4-dihydroxyphenyl)-pyruvic acid, 3-(3,4-dihydroxyphenyl)-lactic acid, dehydrogenase and rosmarinic acid synthase; and
recycling the unreacted 3-(3,4-dihydroxyphenyl)-pyruvic acid, 3-(3,4-dihydroxyphenyl)-lactic acid, dehydrogenase and rosmarinic acid synthase to the reaction mixture.

9. The process as claimed in claim 8, wherein the 3-(3,4-dihydroxyphenyl)-lactic acid is formed in the presence of D-hydroxyisocaproate dehydrogenase.

10. The process as claimed in claim 8, wherein the caffeoyl-coenzyme A is regenerated in situ by the presence of caffeic acid, ATP and CoA ligase.

11. The process as claimed in claim 8, wherein the caffeoyl-coenzyme A is regenerated in situ by the presence of caffeic acid, ATP and CoA ligase, and ATP is regenerated at the same time.

12. The process as claimed in claim 8, wherein the rosmarinic acid synthesis is carried out continuously in two stages by forming 3-(3,4-dihydroxyphenyl)-lactic acid from ketodopa in a first ultrafiltration cell and reacting the product stream from the first cell with caffeoyl-CoA, and simultaneously regenerating caffeoyl-CoA in a second ultrafiltration cell, to produce rosmarinic acid, which is isolated from the product stream of the second cell.

13. The process as claimed in claim 8, wherein ATP is regenerated with acetyl phosphate and acetylkinase.

14. The process as claimed in claim 8, wherein 3-(3,4-dihydroxyphenyl)-lactic acid and rosmarinic acid are formed simultaneously in the same reaction mixture.

15. The process as claimed in claim 1, wherein 3-(3,4-dihydroxyphenyl)-lactic acid and rosmarinic acid are formed simultaneously in the same reaction mixture.

* * * * *